(12) United States Patent
Rehnke

(10) Patent No.: US 11,844,686 B2
(45) Date of Patent: *Dec. 19, 2023

(54) IN VIVO TISSUE ENGINEERING DEVICES, METHODS AND REGENERATIVE AND CELLULAR MEDICINE EMPLOYING SCAFFOLDS MADE OF ABSORBABLE MATERIAL

(71) Applicant: Bard Shannon Limited, Humacao, PR (US)

(72) Inventor: Robert D. Rehnke, St. Petersburg, FL (US)

(73) Assignee: Bard Shannon Limited, Humacao, PR (US)

( * ) Notice: Subject to any disclaimer, the term of this patent is extended or adjusted under 35 U.S.C. 154(b) by 311 days.

This patent is subject to a terminal disclaimer.

(21) Appl. No.: 17/236,155

(22) Filed: Apr. 21, 2021

(65) Prior Publication Data

US 2021/0290363 A1 Sep. 23, 2021

Related U.S. Application Data

(63) Continuation of application No. 16/827,030, filed on Mar. 23, 2020, now Pat. No. 11,638,640.

(51) Int. Cl.
*A61F 2/12* (2006.01)
*A61L 27/36* (2006.01)
*A61F 2/00* (2006.01)

(52) U.S. Cl.
CPC .......... *A61F 2/12* (2013.01); *A61L 27/3604* (2013.01); *A61F 2002/0081* (2013.01);
(Continued)

(58) Field of Classification Search
CPC .............. A61F 2/12; A61F 2002/0081; A61F 2210/0004; A61F 2230/0069;
(Continued)

(56) References Cited

U.S. PATENT DOCUMENTS 4,470,160 A 9/1984 Cavan
5,092,882 A 3/1992 Lynn et al.
(Continued)

FOREIGN PATENT DOCUMENTS

CN 105142572 A 12/2015
EP 2 762 172 B1 6/2015
(Continued)

OTHER PUBLICATIONS

International Preliminary Report on Patentability dated Oct. 8, 2022, in connection with International Application No. PCT/US2020/057329.
(Continued)

*Primary Examiner* — Suzette J Gherbi
(74) *Attorney, Agent, or Firm* — Wolf, Greenfield & Sacks, P.C.

(57) ABSTRACT

Tissue engineering devices and methods employing scaffolds made of absorbable material for use in the human body for tissue genesis and regenerative and cellular medicine including breast reconstruction and cosmetic and aesthetic procedures and supplementing organ function in vivo.

20 Claims, 11 Drawing Sheets

(52) U.S. Cl.
CPC .......... *A61F 2210/0004* (2013.01); *A61F 2230/0069* (2013.01); *A61F 2230/0071* (2013.01); *A61F 2240/002* (2013.01); *A61F 2250/0023* (2013.01)

(58) Field of Classification Search
CPC ........ A61F 2230/0071; A61F 2240/002; A61F 2250/0023; A61L 27/3604
See application file for complete search history.

(56) References Cited

U.S. PATENT DOCUMENTS

| | | |
|---|---|---|
| 5,116,370 A | 5/1992 | Foglietti |
| 5,147,398 A | 9/1992 | Lynn et al. |
| 5,236,454 A | 8/1993 | Miller |
| 5,356,432 A | 10/1994 | Rutkow et al. |
| 5,716,404 A | 2/1998 | Vacanti et al. |
| 5,716,408 A | 2/1998 | Eldridge et al. |
| 5,916,554 A | 6/1999 | Dionne et al. |
| 6,055,989 A | 5/2000 | Rehnke |
| 6,161,034 A | 12/2000 | Burbank et al. |
| 6,210,439 B1 | 4/2001 | Firmin et al. |
| 6,425,924 B1 | 7/2002 | Rousseau |
| 6,548,569 B1 | 4/2003 | Williams et al. |
| 6,730,252 B1 | 5/2004 | Teoh et al. |
| 6,755,867 B2 | 6/2004 | Rousseau |
| 6,867,247 B2 | 3/2005 | Williams et al. |
| 6,875,233 B1 | 4/2005 | Turner |
| 6,902,932 B2 | 6/2005 | Altman et al. |
| 7,081,135 B2 | 7/2006 | Smith |
| 7,179,883 B2 | 2/2007 | Williams et al. |
| 7,208,222 B2 | 4/2007 | Rolfe et al. |
| 7,268,205 B2 | 9/2007 | Williams et al. |
| 7,846,728 B2 | 12/2010 | Brooks et al. |
| 7,857,829 B2 * | 12/2010 | Kaplan .............. A61B 17/1146 606/228 |
| 7,875,074 B2 | 1/2011 | Chen et al. |
| 7,998,152 B2 | 8/2011 | Frank |
| 7,998,735 B2 | 8/2011 | Morrison et al. |
| 8,034,270 B2 | 10/2011 | Martin et al. |
| 8,066,691 B2 | 11/2011 | Khouri |
| 8,388,693 B2 | 3/2013 | Doucet et al. |
| 8,425,600 B2 | 4/2013 | Maxwell |
| 8,556,988 B2 | 10/2013 | Amato et al. |
| 8,728,159 B2 | 5/2014 | Kim |
| 8,747,468 B2 | 6/2014 | Martin et al. |
| 8,758,657 B2 | 6/2014 | Martin et al. |
| 8,858,628 B2 * | 10/2014 | Rigotti ................... A61B 90/02 623/8 |
| 8,858,629 B2 | 10/2014 | Moses et al. |
| 9,014,787 B2 | 4/2015 | Stubbs et al. |
| 9,028,526 B2 | 5/2015 | Khouri |
| 9,125,719 B2 | 9/2015 | Martin et al. |
| 9,180,001 B2 | 11/2015 | Bowley |
| 9,199,002 B2 | 12/2015 | Mao et al. |
| 9,199,092 B2 | 12/2015 | Strubbs et al. |
| 9,326,840 B2 | 5/2016 | Mortarino |
| 9,326,841 B2 | 5/2016 | Martin et al. |
| 9,333,066 B2 | 5/2016 | Martin et al. |
| 9,345,563 B2 | 5/2016 | Hamlin et al. |
| 9,480,780 B2 | 11/2016 | Martin et al. |
| 9,498,195 B2 | 11/2016 | Schutt et al. |
| 9,498,197 B2 | 11/2016 | Peters et al. |
| 9,532,867 B2 | 1/2017 | Felix |
| 9,549,812 B2 | 1/2017 | Shetty |
| 9,555,155 B2 | 1/2017 | Ganatra et al. |
| 9,585,744 B2 | 3/2017 | Moses et al. |
| 9,603,698 B2 | 3/2017 | Kerr et al. |
| 9,615,915 B2 | 4/2017 | Lebovic et al. |
| 9,636,211 B2 | 5/2017 | Felix et al. |
| 9,655,715 B2 | 5/2017 | Limem et al. |
| 9,713,519 B2 | 7/2017 | Horton et al. |
| 9,713,524 B2 | 7/2017 | Glicksman |
| 9,763,770 B2 * | 9/2017 | Lee .................. A61B 17/06166 |
| 9,913,711 B2 * | 3/2018 | Rehnke ..................... A61F 2/12 |
| 9,943,393 B2 | 4/2018 | Martin et al. |
| 9,962,250 B2 | 5/2018 | Priewe et al. |
| 9,974,644 B2 | 5/2018 | Khouri |
| 9,980,809 B2 | 5/2018 | Lebovic et al. |
| 9,987,114 B2 | 6/2018 | Criscuolo et al. |
| 10,028,818 B2 | 7/2018 | Felix et al. |
| 10,058,417 B2 | 8/2018 | Limem et al. |
| 10,286,114 B2 | 5/2019 | Hermann et al. |
| 10,413,381 B2 | 9/2019 | Hermann et al. |
| 10,433,943 B2 | 10/2019 | Towfigh |
| 10,595,986 B2 * | 3/2020 | Rehnke ..................... A61F 2/12 |
| 10,709,539 B2 | 7/2020 | Mathisen |
| 10,716,573 B2 | 7/2020 | Connor |
| 10,722,336 B2 | 7/2020 | Mathisen et al. |
| 10,799,336 B2 | 10/2020 | Hutmacher et al. |
| 10,820,980 B2 | 11/2020 | Criscuolo et al. |
| 11,213,394 B2 | 1/2022 | Yang et al. |
| 11,426,269 B2 | 8/2022 | Paydar et al. |
| 11,452,511 B2 | 9/2022 | Barbot et al. |
| 11,571,271 B2 | 2/2023 | Martinez et al. |
| 11,602,426 B2 | 3/2023 | Weems et al. |
| 11,628,054 B2 | 4/2023 | Greenhalgh et al. |
| 11,638,640 B2 * | 5/2023 | Rehnke ............... A61L 27/3604 623/8 |
| 11,642,207 B2 | 5/2023 | Young |
| 11,642,215 B2 | 5/2023 | Yang et al. |
| 11,648,011 B2 | 5/2023 | Kassab et al. |
| 11,654,027 B2 | 5/2023 | Crabb et al. |
| 2001/0027347 A1 | 10/2001 | Rousseau |
| 2002/0077701 A1 | 6/2002 | Kuslich |
| 2003/0027332 A1 | 2/2003 | Lafrance et al. |
| 2007/0208377 A1 | 9/2007 | Kaplan et al. |
| 2008/0004657 A1 | 1/2008 | Obermiller et al. |
| 2008/0097601 A1 | 4/2008 | Codori-Hurff et al. |
| 2008/0287970 A1 | 11/2008 | Amato et al. |
| 2008/0300681 A1 | 12/2008 | Rigotti et al. |
| 2009/0012483 A1 | 1/2009 | Blott et al. |
| 2009/0036997 A1 | 2/2009 | Bayon et al. |
| 2009/0125107 A1 | 5/2009 | Maxwell |
| 2009/0192530 A1 | 7/2009 | Adzich et al. |
| 2009/0198329 A1 | 8/2009 | Kesten et al. |
| 2009/0234459 A1 | 9/2009 | Sporring |
| 2010/0023029 A1 | 1/2010 | Young |
| 2010/0168808 A1 | 7/2010 | Citron |
| 2010/0191330 A1 | 7/2010 | Lauryssen et al. |
| 2010/0280532 A1 | 11/2010 | Gingras |
| 2011/0009960 A1 | 1/2011 | Altman et al. |
| 2011/0224703 A1 | 9/2011 | Mortarino |
| 2011/0257665 A1 | 10/2011 | Mortarino |
| 2011/0301717 A1 | 12/2011 | Becker |
| 2012/0004723 A1 | 1/2012 | Mortarino et al. |
| 2012/0010706 A1 | 1/2012 | Schuessler |
| 2012/0022646 A1 | 1/2012 | Mortarino et al. |
| 2012/0029537 A1 | 2/2012 | Mortarino |
| 2012/0150204 A1 | 6/2012 | Mortarino et al. |
| 2012/0185041 A1 | 7/2012 | Mortarino et al. |
| 2012/0221105 A1 | 8/2012 | Altman et al. |
| 2013/0006279 A1 | 1/2013 | Mortarino |
| 2013/0103149 A1 | 4/2013 | Altman et al. |
| 2013/0190783 A1 | 7/2013 | Noda et al. |
| 2013/0253645 A1 | 9/2013 | Kerr et al. |
| 2013/0304098 A1 | 11/2013 | Mortarino |
| 2014/0081076 A1 | 3/2014 | Schutt |
| 2014/0088700 A1 | 3/2014 | Mortarino et al. |
| 2014/0128891 A1 | 5/2014 | Astani-Matthies et al. |
| 2014/0163678 A1 | 6/2014 | Van Epps |
| 2014/0222146 A1 | 8/2014 | Moses et al. |
| 2014/0257481 A1 | 9/2014 | Brooks et al. |
| 2014/0277000 A1 | 9/2014 | Mortarino et al. |
| 2015/0112434 A1 | 4/2015 | Felix |
| 2015/0150681 A1 | 6/2015 | Ricci et al. |
| 2015/0223928 A1 | 8/2015 | Limem |
| 2015/0351889 A1 | 12/2015 | Reddy et al. |
| 2015/0351900 A1 | 12/2015 | Glicksman |
| 2016/0022416 A1 | 1/2016 | Felix |
| 2016/0242899 A1 * | 8/2016 | Lee ..................... A61F 2/12 |
| 2017/0189016 A1 | 7/2017 | Gross |
| 2017/0196672 A1 | 7/2017 | Guterman |
| 2017/0224471 A1 | 8/2017 | Rehnke |

(56) References Cited

U.S. PATENT DOCUMENTS

| | | | |
|---|---|---|---|
| 2017/0231749 | A1 | 8/2017 | Perkins et al. |
| 2017/0258574 | A1 | 9/2017 | Hutmacher et al. |
| 2017/0348090 | A1 | 12/2017 | Saint |
| 2017/0360555 | A1 | 12/2017 | Glicksman |
| 2018/0206978 | A1 | 7/2018 | Rehnke |
| 2018/0214262 | A1 | 8/2018 | Diaz |
| 2018/0296313 | A1 | 10/2018 | Mathisen et al. |
| 2019/0060520 | A1 | 2/2019 | Pelling et al. |
| 2019/0343620 | A1 | 11/2019 | Mlodinow et al. |
| 2020/0222175 | A1 | 7/2020 | Danze et al. |
| 2020/0222176 | A1* | 7/2020 | Hsieh ............... A61L 27/20 |
| 2020/0268498 | A1* | 8/2020 | Reddy ............... A61F 2/0063 |
| 2020/0268503 | A1 | 8/2020 | Rehnke |
| 2020/0375726 | A1 | 12/2020 | Limem et al. |
| 2021/0236264 | A1 | 8/2021 | Rehnke |
| 2021/0236265 | A1 | 8/2021 | Rehnke |
| 2021/0236266 | A1 | 8/2021 | Rehnke |
| 2021/0236267 | A1 | 8/2021 | Rehnke |
| 2021/0251742 | A1 | 8/2021 | Rehnke |
| 2021/0290361 | A1* | 9/2021 | Rehnke ............... A61F 2/12 |
| 2021/0290362 | A1* | 9/2021 | Rehnke ............... A61F 2/0063 |
| 2021/0290364 | A1 | 9/2021 | Rehnke |
| 2021/0290365 | A1* | 9/2021 | Rehnke ............... A61F 2/0063 |
| 2021/0290366 | A1* | 9/2021 | Rehnke ............... A61F 2/12 |
| 2021/0369912 | A1 | 12/2021 | Toro Estrella et al. |
| 2021/0401436 | A1 | 12/2021 | Kassab et al. |
| 2022/0233299 | A1 | 7/2022 | Bruhn et al. |
| 2022/0370184 | A1 | 11/2022 | Bruhn et al. |
| 2023/0118855 | A1 | 4/2023 | Gifford, III et al. |
| 2023/0146295 | A1 | 5/2023 | Chhaya et al. |
| 2023/0172842 | A1 | 6/2023 | Shiah et al. |

FOREIGN PATENT DOCUMENTS

| | | |
|---|---|---|
| FR | 2 682 284 A1 | 4/1993 |
| JP | 2005-137398 A1 | 6/2005 |
| JP | 4296399 B2 | 7/2009 |
| TW | M577719 U | 5/2019 |
| WO | WO 2012/094057 A1 | 7/2012 |
| WO | WO 2018/078489 A1 | 5/2018 |
| WO | WO 2021/188975 A2 | 9/2021 |

OTHER PUBLICATIONS

International Search Report and Written Opinion dated Feb. 8, 2021 in connection with International Application No. PCT/US2020/057329.

Adams et al., Clinical Use of GalaFLEX in Facial and Breast Cosmetic Plastic Surgery. Aesthetic Surgery Journal, 2016, vol. 36 (52), pp. 523-532.

Bard Davol Inc., Phasix Plug and Patch. product catalog, obtained from C.R. Bard, Inc. website (www. crbard.com), copyright 2013, 4 pgs., US.

Bard Davol Inc., Phasix Plug and Patch. screenshot of C.R. Bard, Inc. website page (www.crbard.com) 2013, 1 pg., US.

Chhaya et al., Transformation of Breast Reconstruction via Additive Biomanufacturing. Scientific Reports Jun. 15, 2016, 12 pgs., US.

Deeken et al., Characterization of the Mechanical Strength, Resorption Properties, and Histologic Characteristics of a Fully Absorbable Material (Poly-4-hydroxybutyrate—PHASIX Mesh) in a Porcine Model of Hernia Repair. ISRN Surgery Hindawi Publishing Corp., vol. 2013, Article Id 238067, 12 pages, Mar.-Apr. 2013.

Findlay et al., Tissue-Engineered Breast Reconstruction: Bridging the Gap toward Large-Volume Tissue Engineering in Humans. PRS Journal, Obrien Institute, the University of Melbourne Department of Surgery, accepted for publication Jun. 20, 2011, pp. 1206-1215.

Harman et al., A New Method for Partial Breast Reconstruction: 3-Year New Zealand Experience, PRS Journal, vol. 143, No. 1, pp. 49-52, Jan. 2019.

Khouri et al., Megavolume Autologous Fat Transfer: Part I. Theory and Principles. PRS Journal, vol. 133, No. 3, Mar. 2014, pp. 550-557.

Martin et al., Medical applications of poly-4-hydroxybutyrate: a strong flexible absorbable biomaterial. Elsevier Biochemical Engineering Journal 16, Dec. 9, 2003 pp. 97-105.

Morrison et al., Creation of a Large Adipose Tissue Construct in Humans Using a Tissue-engineering Chamber: A Step Forward in the Clinical Application of Soft Tissue Engineering. EbioMedicine 6 (2016), pp. 238-245, available online Mar. 23, 2016.

Qin et al., External vol. Expansion Up-Regulates CXCL12 Expression and Enhances Mesenchymal Stromal Cell Recruitment toward Expanded Prefabricated Adipose Tissue in Rats. PRSJournal, Department of Plastic and Cosmetic Surgery, Nanfang Hospital, Southern Medical University; accepted for publication Oct. 19, 2017, pp. 526e-537e.

ReconSurgicalVideos on YouTube, Immediate Breast Reconstruction Without Implants, Skin and Nipple Sparing Mastectomy, Internal Mastopexy Purse String, Dr. Robert D. Rehnke (Inventor) and Dr. John Clarke, uploaded to YouTube Apr. 9, 2017, URL:https://www.youtube.com/watch?v=dR_IXLygxi8, screenshots 0:02, 0:05, 0:24, 0:35, 1:34, 2:57, 3:12, 3:29, 3:47, 4:11, 4:29.

ReconSurgicalVideos on YouTube, MIS Mastectomy and Immediate Reconstruction with P4HB Scaffold and Fat Grafting, Dr. Robert Rehnke (Inventor), uploaded to YouTube, Mar. 25, 2016, URL: https://www.youtube.com/watch?v=4QzYsFAA7Jc, screen shots 0:07,4:52, 6:22, 9:38, 10:03, 11:18, 11:42, 11:58, 12:24.

ReconSurgicalVideos on YouTube, Organic Breast Reconstruction with Autologous Fat Graft, Biodegradable Scaffold, Dr. Robert Rehnke (Inventor), uploaded to YouTube, Mar. 28, 2017, URL: https://www.youtube.com/watch?v=MyzhDBQNneA, screen shots 0:01,0:05, 5:56, 6:06.

ReconSurgicalVideos on YouTube, P4HB 3-D Solid Implant Immediate Breast Reconstruction. John Clarke, MD and Robert Rehnke, MD (Inventor), uploaded to YouTube, Feb. 20, 2016, URL: https://www.youtube.com/watch?v=swbEcrt7RTk, screen shots 0:01,1:15, 1:30, 2:10, 8:58, 9:19.

Rehnke et al., Anatomy of the Superficial Fascia System of the Breast: A Comprehensive Theory of Breast Fascial Anatomy. PRS Journal, vol. 142, No. 5, pp. 1135-1144, Nov. 2018.

Schusterman et al., Breast Reconstruction Using a 3-dimensional Absorbable Mesh Scaffold and Autologous Fat Grafting A Composite Strategy Using Tissue Engineering Principles. PRS Global Open, International Open Surgeons, PRS Access Aug. 7, 2019, published online Sep. 10, 2019, pp. 1-2.

Sharma et al., Adipocyte-derived basement membrane extract with biological activity: applications in hepatocyte functional augmentation in vitro. The FASEB Journal Research Communication article fj.09-135095. Published online Mar. 16, 2010, pp. 1-12.

Williams et al., The History of GalaFLEX P4HB Scaffold. Aesthetic Surgery Journal, 2016, vol. 36(52), pp. 533-542.

Zhan et al., Adipose-Derived Stem Cell Delivery for Adipose Tissue Engineering: Current Status and Potential Applications in a Tissue Engineering Chamber Model. Springer Science+Business Media New York 2016, Stem Cell Rev and Rep, 2016, vol. 12, pp. 484-491.

Chinese Office Action dated Nov. 4, 2022, in connection with Chinese Application No. 202080050699.6.

\* cited by examiner

IN VIVO TISSUE ENGINEERING DEVICES, METHODS AND REGENERATIVE AND CELLULAR MEDICINE EMPLOYING SCAFFOLDS MADE OF ABSORBABLE MATERIAL

RELATED APPLICATIONS

This application is a continuation of U.S. patent application Ser. No. 16/827,030, filed Mar. 23, 2020, which is incorporated herein by reference in its entirety.

BACKGROUND OF THE INVENTION

Field of the Invention

The present invention relates to tissue engineering devices and methods employing scaffolds made of absorbable material implanted in the human body and use of such devices and methods in breast procedures, such as breast reconstruction, augmentation, mastopexy and reduction, in various cosmetic and aesthetic procedures involving tissue shaping and adipogenesis and in regenerative and cellular medicine to enhance and supplement organ function in vivo.

BRIEF DISCUSSION OF RELATED ART

Breast implants are commonly used to replace breast tissue that has been removed due to cancer and are also commonly used for breast augmentation. Most breast implants to replace the corpus mammae after a mastectomy are either saline-filled or silicone gel-filled. Acellular matrices are used mainly for lower pole breast coverage and the shaping of reconstructed breasts. These prior art breast implants have many disadvantages and frequently cause tissue necrosis and capsular contracture. Where the breast surgery is a partial mastectomy (frequently called a lumpectomy) implantable devices have been proposed for placement in the surgical defect. One such device called the BioZorb implant is marketed by Focal Therapeutics, Inc. and includes a rigid bioabsorbable body formed by framework elements producing a non-contiguous external perimeter, such as a coil. The result is that the device does not fill the surgical defect in many instances and, thus, does not achieve a consistently high quality aesthetic appearance which is the outcome desired following lumpectomy. Additionally, the device does not adequately stent the defect in smaller breasted, thin women and in such cases does not promote gradual healing of the lumpectomy space without scar contracture. U.S. Pat. Nos. 9,615,915 and 9,980,809 to Lebovic et al and U.S. Pat. No. 10,413,381 to Hermann et al are representative of these implants which have the disadvantage of not providing the cosmetic/aesthetic desired results but rather are dependent upon the size of the defect.

Autologous fat grafting is an increasingly common procedure in both aesthetic and reconstructive surgery. Adipogenesis from the grafted autologous fat serves many purposes including, but not limited to, shaping and support of soft tissue, such as in the breast and the buttocks (gluteus), and in in vivo tissue engineering.

In breast reconstruction and augmentation surgical procedures, autologous fat grafting is an extremely important step, and enhanced vascularization of the fat is important for improved fat survival. Autologous fat grafting for breast procedures typically involves aspirating fat from the patient with a syringe and injecting the aspirated fat into the soft breast tissue. In the past, attempts to increase vascular density of the injected fat have involved the use of structures to provide volume expansion to assist the fat grafting. Breast procedures and devices employing structures to provide distractive forces are exemplified by U.S. Pat. Nos. 8,066,691, 9,028,526 and 9,974,644 to Khouri and U.S. Patent Application Publication No. 2008/03006812 to Rigotti et al and are also described in an article entitled "Megavolume Autologous Fat Transfer: Part I. Theory and Principles" authored by Khouri et al, PRS Journal, Volume 133, Number 3, March 2014, pages 550-557. The prior art attempts to improve fat survival have not been successful from a practical standpoint and have had many disadvantages, primarily the need to remove the structures after the surgical procedure.

Many efforts have been made in medicine to replace pharmaceuticals with cellular therapies and to use tissue engineering and regenerative medicine to replace synthetic replacement parts. Science has attempted in the past to engineer replacement parts and organs for the human body. Most efforts have focused on the use of stem cells and decellularized allograft organs. Unfortunately, these attempts and associated therapies have not succeeded in clinical practice, largely due to the problem of developing vascular supply to the large volumes of tissue required for these therapies. Prior art attempts to accomplish in vivo tissue engineering have failed to take advantage of the self-organizing properties of healing tissues. Under the influence of macrophage type-2 inflammation, healing tissues under the influence of proteins, like cytokines and extra cellular matrix proteins, have the ability to organize themselves into biologically authentic order and structure. This activity requires physical support and a blood supply, on a fractal order, and the prior art has failed to provide these requirements.

In the past, attempts have been made to use tissue engineering techniques to combine stem cells and exomes employing scaffolds to overcome the problem of donor tissue scarcity. The attempts have not beneficially affected the function (parenchyma) of the organ due to the inability to integrate fully functioning vascular architectures into the engineered construct. Thus, there has been a need for tissue engineering devices for use in organ generation and/or supplementing the function of organs in the human body.

SUMMARY OF THE INVENTION

Absorbable" material means a material that is degraded in the body. It is noted that the terms "absorbable", "resorbable", and "degradable" are used in the literature interchangeably with or without the prefix "bio". Accordingly, absorbable material as used herein means a material broken down and gradually absorbed, excreted or eliminated by the body whether the degradation is due to hydrolysis or metabolic processes. A preferred long term absorbable material for use with the present invention is Poly-4-Hydroxybutyrate, which is commonly referred to as P4HB, and is manufactured by Tepha, Inc., Lexington, Massachusetts. P4HB is typically available in sheets which are referred to as two-dimensional materials and is also available as three-dimensional materials which can be shaped by molding. Absorbable materials useful to make the scaffold of the tissue engineering device according to the present invention are frequently referred to as biodegradable polymers such as the following: polylactic acid, polyglycolic acid and copolymers and mixtures thereof such as poly(L-lactide) (PLLA), poly(D,L-lactide) (PLA), polyglycolic acid or polyglycolide (PGA), poly(L-lactide-co-D,L-lactide)

(PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), poly(D,L-lactide-co-caprolactone) (PLA/PCL) and poly(glycolide-co-caprolactone) (PGA/PCL); polyhydroxyalkanoates, poly(oxa) esters, polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone co-butylacrylate, polyhydroxybutyrate (PH BT) and copolymers of polyhydroxybutyrate, poly(phosp-hazene), poly(phosphate ester), poly(amino acid), polydepsipeptides, maleic anhydride copolymers, polyiminocarbonates, poly[(97.5% dimethyl-trimethylene carbonate)-co-(s.5% trimethylene carbonate)], poly(orthoesters)tyrosine-derived, polyarylates, tyrosine-derived polycarbonates, tyrosine-derived polyiminocarbonates, tyrosine-derived polyphosphonates, polyethylene oxide, polyethylene glycol (PEG), polyalkylene oxides (PAO), hydroxypropylmethyl-cellulose, polysaccharides such as hyaluronic acid, chitosan and regenerate cellulose, and proteins such as gelatin and collagen, and mixtures and copolymers thereof, among others as well as PEG derivatives or blends of any of the foregoing. Desirably, polymeric materials can be selected for these systems and methods that have good strength retention, such as polydioxanone, silk-based polymers and copolymers, poly4-hydroxybutyrates, and the like.

The present invention overcomes the disadvantages of the prior art by configuring a scaffold made of porous absorbable material to provide physical support for a large volume of tissue, including autologous fat, in a plurality of tissue engineering chambers arranged around a core which can be hollow to accommodate blood vessels. In one embodiment, the tissue engineering device of the present invention employs a scaffold made of a mesh absorbable material formed of a mono-filament polymer knitted mesh which provides a biologic scaffold matrix for cell attachment and protein organization. The matrix is invaded by capillaries, in a granulation type process that transforms the mesh into engineered fascia. The absorbable mesh material structure has a plurality of partially open tissue engineering chambers. The chambers can be formed by folds in one or more sheets of absorbable material and arranged radially around a central core. The chambers can be segmented and/sub-segmented to increase the surface area of the scaffold. The tissue engineering device of the present invention has a shape to be implanted in an anatomical space in fascia of the human body, and the tissue engineering chambers have an aggregate surface area greater than the fascia surface area in the anatomical space. The anatomical space can be a defect created during surgery in superficial fascia, for example in the breast, or in deep fascia adjacent an organ, for example the pancreas, kidneys or liver, when the tissue engineering device is employed for recellularization with functional parenchymal cells. With respect to the pancreas, the tissue engineering device of the present invention can be used to replace insulin-producing islet beta cells destroyed in some types of diabetes. With respect to the liver, the tissue engineering device of the present invention can be used to produce a plentiful source of hepatocytes for regenerating liver tissue and treating metabolic diseases.

In another embodiment of the present invention, the scaffold has an open or hollow core designed for receiving a vascular pedicle having an appropriately sized artery with its vena comitans, fascia and associated fat such that a large volume of engineered tissue is broken down into fractal units of tissue with its own circulation. The radial arrangement of tissue engineering chambers, which can be formed of segments and associated sub-segments, surround the core and break down the large volume of tissue into units approximately 5 cc in volume, which is the volume whereby self-organizing tissues sprout at the terminus of capillary growth. The engineering of large volumes of vascularized living tissue is accomplished with the present invention by a combination of man-made and designed structures and in vivo biologic cells and proteins that organize themselves into healthy tissues.

The tissue engineering devices and methods according to the present invention can be utilized in the body to encourage rapid tissue ingrowth for various reconstructive and cosmetic procedures relating to tissue grafting, particularly, autologous fat in soft tissue areas including, but not limited to, the breast and the buttocks. In the past, autologous fat grafting has involved aspirating fat from a patient with a syringe and injecting the aspirated fat into the soft tissue. As noted above, many prior art procedures and/or devices utilized for fat grafting involve application of distractive forces whereas the tissue engineering devices and methods of the present invention obviate the need for such distractive forces by employing scaffolds having tissue engineering chambers radially arranged around a central core to collect and vascularize tissue.

The tissue engineering devices and methods of the present invention employ a scaffold made of absorbable material. In one embodiment, the present invention employs an open-pore knit pattern of absorbable material to encourage rapid tissue ingrowth through the micro-pores of the scaffold.

The scaffold employed in the tissue engineering device of the present invention permits lipoaspirate fatty tissue injected in the tissue engineering chambers to be mixed with the absorbable material thus holding the micro-globules of liposuctioned fat in place in a three-dimensional, scattered fashion to promote vascularization and prevent pooling of the fat which otherwise could lead to necrosis. Additionally, the tissue engineering chambers can be, prior to insertion in the body, coated with substances known to encourage tissue regeneration and then coated with selected tissue cells such as pancreatic islet cells, hepatic cells, or other cells as well as with stem cells and exosomes genetically altered to contain genes for treatment of patient illnesses. The radially arranged tissue engineering chambers provide good neovascularization with mononuclear inflammatory cells and multi-nucleic giant cells as well as adipogenesis on the absorbable material surfaces, in the absorbable material and between the layers of folded absorbable material.

The number of tissue engineering chambers can vary but are normally somewhere between eight and ten thus dividing the greater overall volume of the space for tissue expansion into smaller, subunit spaces. The joining together of the tissue engineering chambers around a central core adds to the stability of the scaffold while minimizing the required mesh absorbable material.

The scaffold of the tissue engineering device of the present invention has multiple points of connection to form a tension system, and fatty tissue is created which will eventually fill the tissue engineering chambers to create a structure that will bend but not break and return to its original equilibrium shape after distorting influences are removed. Advantageously, the absorbable material is a mesh material composed of a loose-knit monofilament, such as an absorbable polyester like Poly-4 Hydroxybutyrate (P4HB) which is a naturally occurring polymer known to have antibacterial properties and induces M2 phase of inflammation leading to tissue regeneration.

Globules of fat and partial globules broken apart by surgical dissection will fall into the tissue engineering chambers which is desirable since the collagen matrix of the fascia system with its capillaries and arterioles are known to be the location of new adipose tissue creation or adipogenic sites. The large surface area of the scaffold provides structure for neovascularization and three-dimensional locations for distribution of priming substances such as liposuction aspirant. In other priming maneuvers, loose knit, microporous material of the scaffold can be coated with proteins known to promote tissue regeneration and can be covered with other chemical compounds. The scaffold can be colonized with undifferentiated stem cell transplants from healthy cells that grow and produce metabolic compounds.

The tissue engineering device scaffolds of the present invention can be fabricated using a wide range of polymer processing techniques. Methods of fabricating the tissue engineering scaffolds include solvent casting, melt processing, fiber processing/spinning/weaving, or other means of fiber forming extrusion, injection and compression molding, lamination, and solvent leaching/solvent casting. One method of fabricating tissue engineering absorbable material scaffolds involves using an extruder such as a Brabender extruder to make extruded tubes.

Another fabrication method involves preparing a nonwoven absorbable material scaffold from fibers produced from the melt or solution and processed into woven or nonwoven sheets. The properties of the sheets can be tailored by varying, for example, the absorbable material, the fiber dimensions, fiber density, material thickness, fiber orientation and method of fiber processing. The sheets can be further processed and formed into hollow tubes.

Another method involves melt or solvent processing a suitable absorbable material into an appropriate mold and perforating the material using a laser or other means to achieve the desired porosity. Other methods include rolling a compression molded absorbable material sheet into a loop and heat sealing. The tissue engineering devices of the present invention can be seeded with cells prior to implantation or after implantation.

The tissue engineering devices and methods of the present invention can be used for in vivo tissue engineering for organs, including the kidneys, pancreas and liver. The absorbable material is a mesh to allow invasion of fibroblasts to produce collagen which wraps around the monofilament fibers of the mesh. Capillaries grow into the mesh bringing circulation to a large three-dimensional space in the mesh engineered fascia. Lipoaspirate is added to self-organize into a stroma in the spaces between the mesh, the stroma being the supportive tissue of the organ consisting of connective tissues and blood vessels. Another added ingredient is stem cells and exosomes which are seeded on the scaffold when it is implanted. The type of stem cell and/or exosome is chosen depending on the function of the organ being engineered. For example, stem cells from adipose tissue or mesenchymal stem cells are appropriate for breast reconstruction. Glomerular stem cells are used for engineering a kidney. Stem cells associated with pancreatic islet cells are used for the pancreas to treat diabetes. The stem cells develop the parenchyma of the organ.

Accordingly, it can be seen that the tissue engineering device of the present invention presents a building block for in vivo organ development (engineering) or supplementation in that the tissue engineering device provides mesh to engineer a supportive fascia which brings vascularity to a large three-dimensional space and stromal cells that are the supportive filler and functional cells of a specific organ in the parenchyma.

Along with the above noted advantages of the present invention in tissue engineering, the present invention has the additional advantages of being used as, essentially, a bio-hybrid organ for hormone replacement therapy to obviate the need for hormone pellets. That is, instead of implanting slowly dissolving pellets to release a set amount of estrogen or testosterone, the tissue engineering device of the present invention can be used to colonize cells that are a part of human body circulation to release the hormones naturally which is particularly advantageous in patients whose increased age has reduced their hormone levels. Similarly, the tissue engineering device of the present invention can be implanted in individuals with hypothyroidism to be the locus for a colony of transplanted cells that produce thyroid hormone. When the tissue engineering device of the present invention is used as a bio-hybrid organ, endocrine cells are generated with the individual's hypothalamus and pituitary glands controlling the amount of hormone production in accordance with their normal function. A pancreatic bio-hybrid tissue engineering device according to the present invention can also allow an islet cell colony to evade attack by the immune system in individuals with Type 1 diabetes. CRISPR technology can be used to take autologous islet cells and disable their NLRC5 gene, and the islet cells can then be implanted in the tissue engineering device allowing the device to function as a bio-hybrid endocrine organ without being attacked by the immune system. Tissue engineering devices of the present invention implanted in the breast do not present the complications of capsular contracture and infection frequently associated with silicone implants used for breast reconstruction in that adipogenesis is enhanced by capillaries from the superficial fascia growing into the open, porous surfaces of the scaffold which have received the small globules of aspirated fat. Thus, healthy tissue with good vascularity is created to avoid infection. When the tissue engineering device of the present invention is implanted following lumpectomy, the spherical-type shape fills the defect and promotes gradual healing of the lumpectomy space without scar contracture while the scaffold acts as a stent preventing wound contracture and scarring and promoting M2 regenerative healing of the lumpectomy defect. The round surface of the spherical-like scaffold minimizes damage to delicate tissue, prevents extrusion and, more completely, approximates the lumpectomy defect than prior art devices.

Other aspects and advantages of the tissue engineering devices and tissue engineering methods of the present invention will become apparent from the following description of the invention taken in conjunction with the accompanying drawings wherein like parts in each of the several figures are identified by the same reference characters.

DETAILED DESCRIPTION OF THE INVENTION

Figure 1:
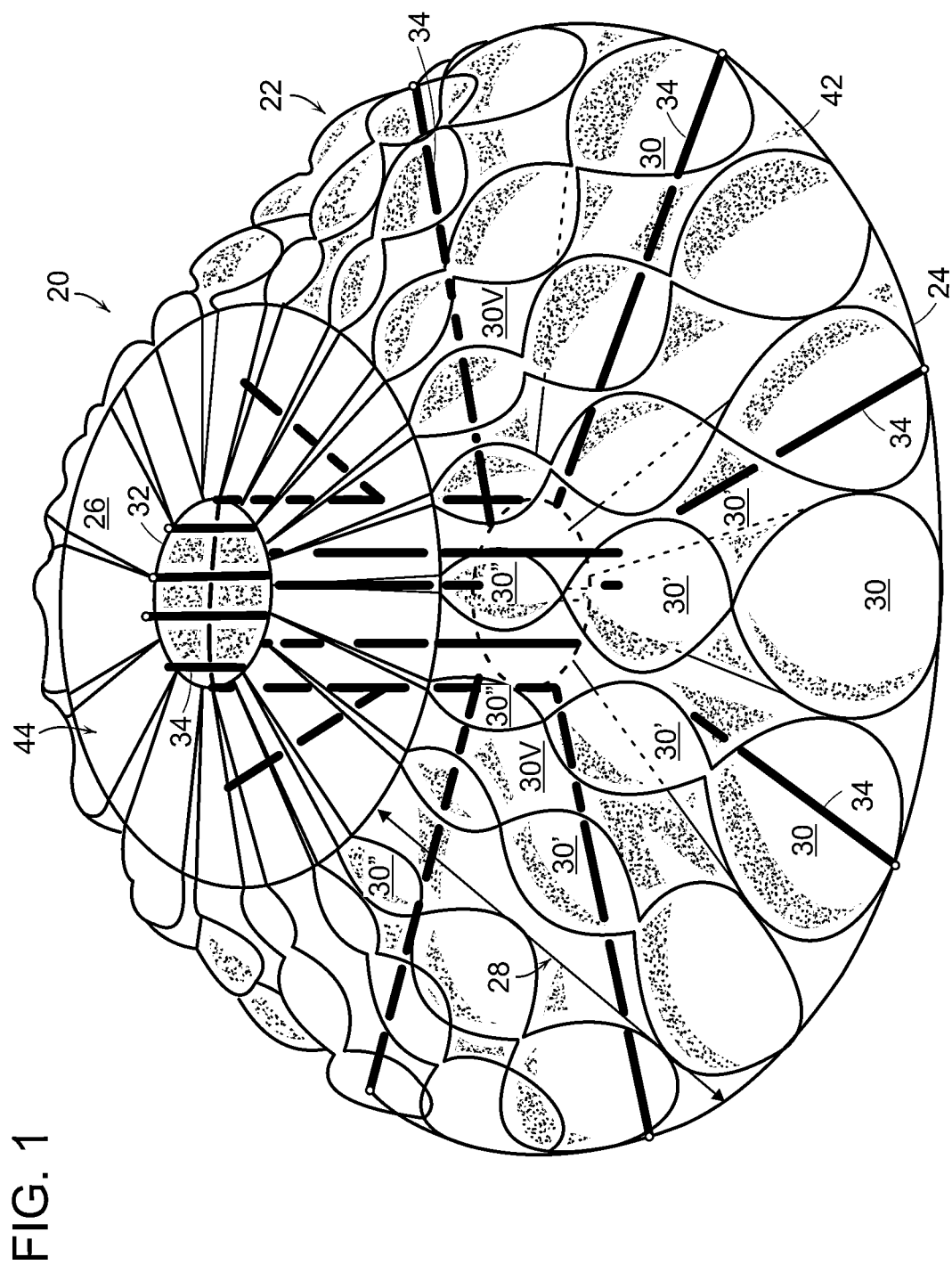
FIG. 1 is a perspective view of an embodiment of the in vivo tissue engineering device of the present invention.
Figure 2:
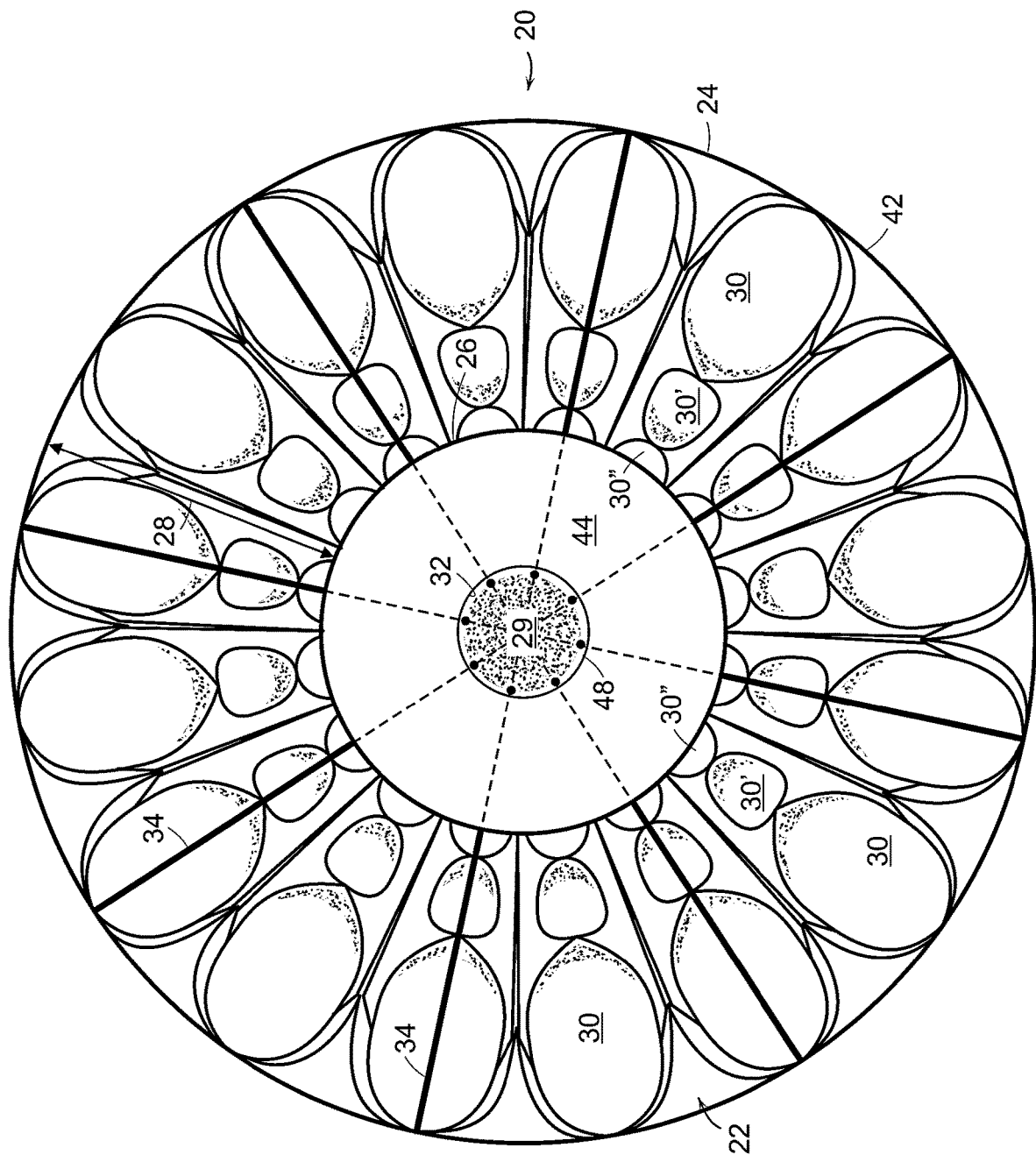
FIG. 2 is a top view of the tissue engineering device of FIG. 1.

An in vivo tissue engineering device 20 according to the present invention is shown in FIGS. 1 and 2 and includes a scaffold 22 made of one or more sheets of mesh absorbable material which is, by nature, porous. The scaffold has a wide base or proximal portion 24, a narrower apex or distal portion 26 and a tapering, sidewall 28 extending between the base portion and the apex portion. The sidewall 28 is formed by a plurality of partially open, tissue engineering chambers 30 such that the sidewall has a rugose configuration formed by pleats or folds of the one or more sheets of absorbable material. The scaffold has a hollow inner region 29 which can be formed by a central core 32 extending between the base portion and the apex portion. If required by size, volume and stability, a plurality of L-shaped tubular struts 34 made of absorbable material can be radially arranged on the scaffold with legs extending through the core and bent 90° to terminate adjacent the perimeter of the base portion. As shown, the scaffold has a truncated geometrical shape designed to be placed in the body in a position where the base portion is adjacent bodily tissue to define a fixation or anchoring location where the scaffold is supported and the apex portion is spaced from the fixation location. When the tissue engineering device is used for breast procedures, such as breast reconstruction or augmentation (e.g. after mastectomy, implant replacement, mastopexy and other breast procedures), the scaffold can have a truncated shape similar to a brassiere cup such that the shape of the scaffold can be considered to be a frustoconical-like or pyramidal-like three-dimensional structure.

Figure 3:
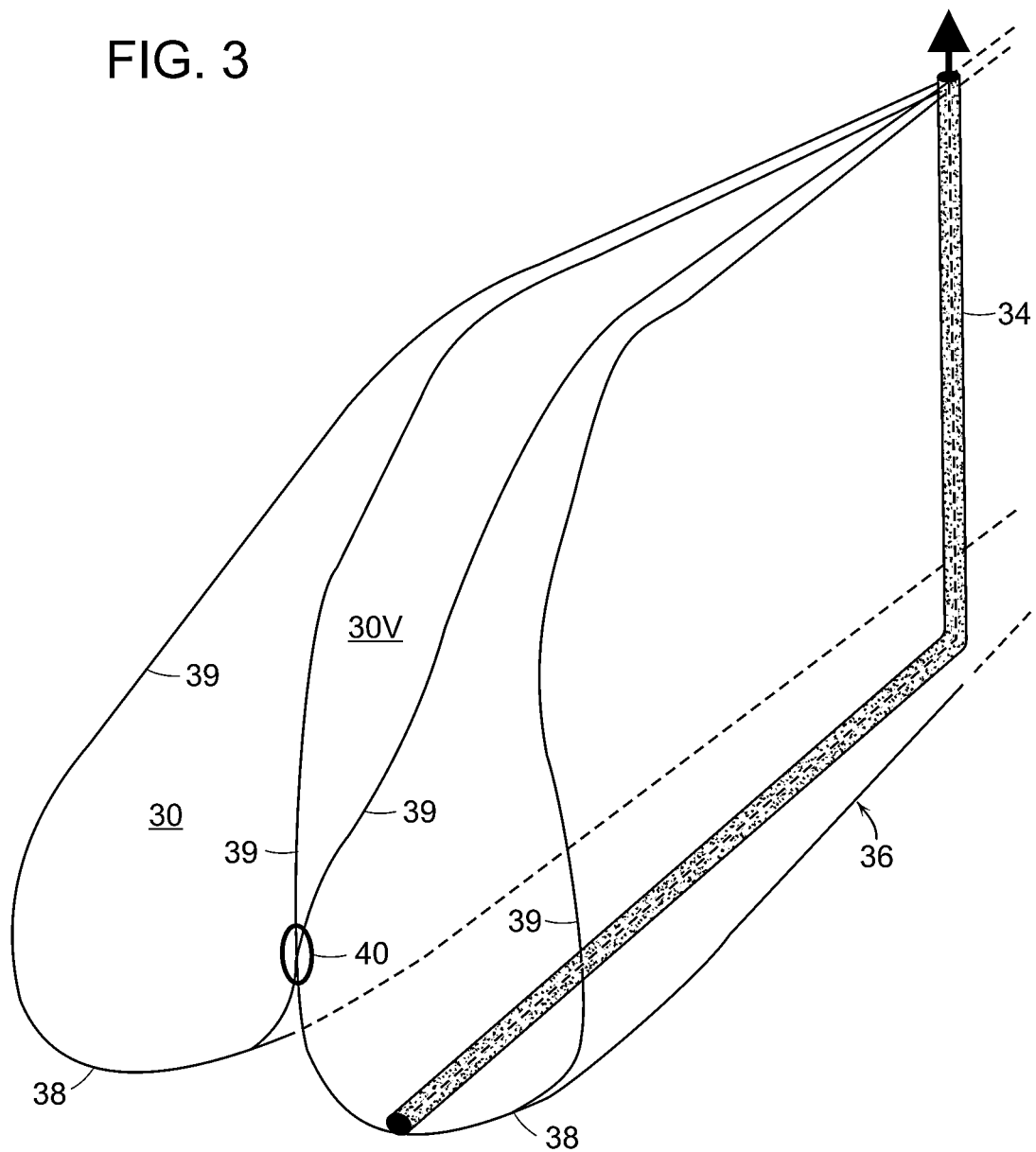
FIG. 3 is a broken perspective view illustrating a method of fabrication of the tissue engineering device of the present invention.
Figure 4:
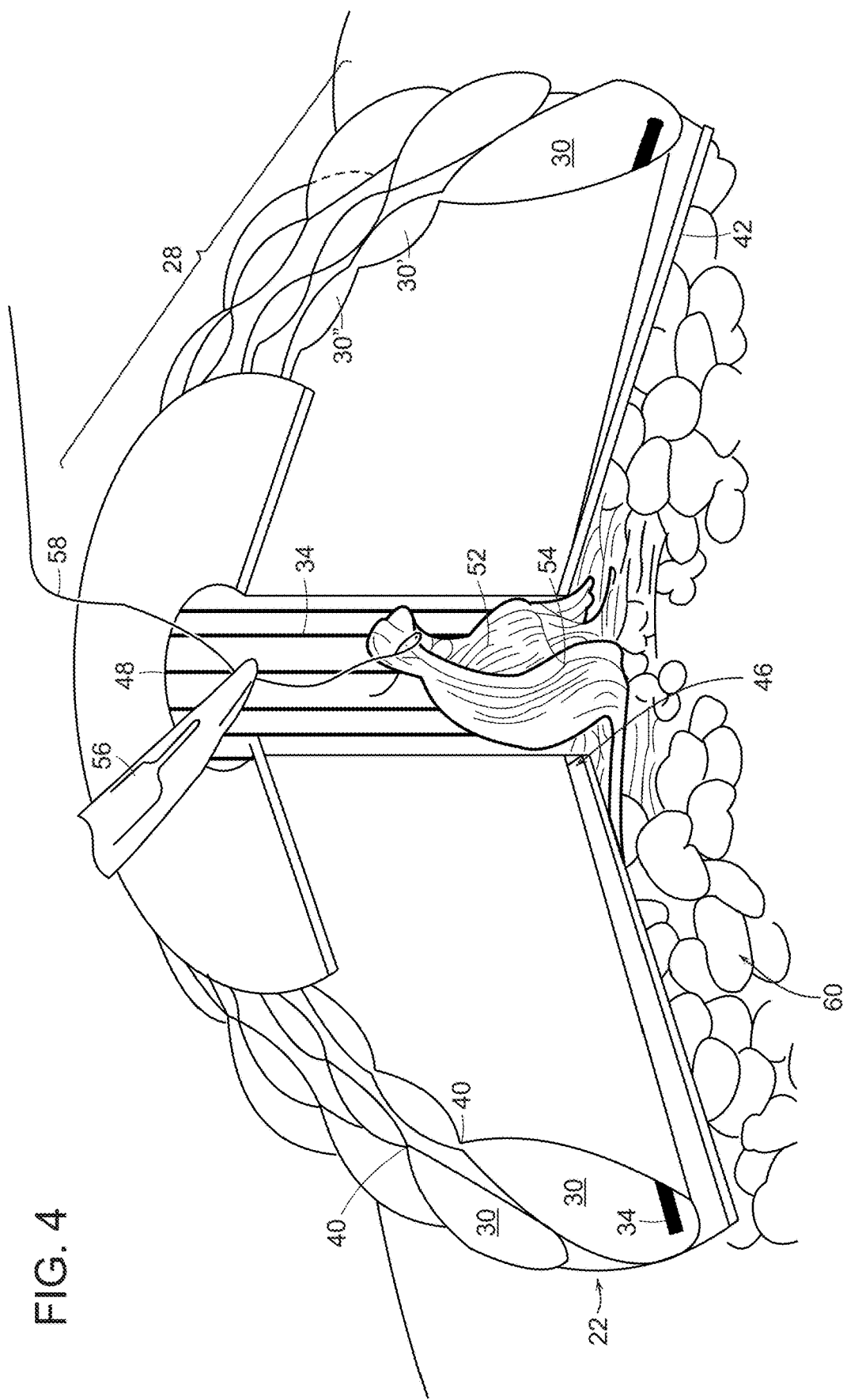
FIG. 4 is a broken perspective view illustrating implant of a tissue engineering device of the present invention.
Figure 5:
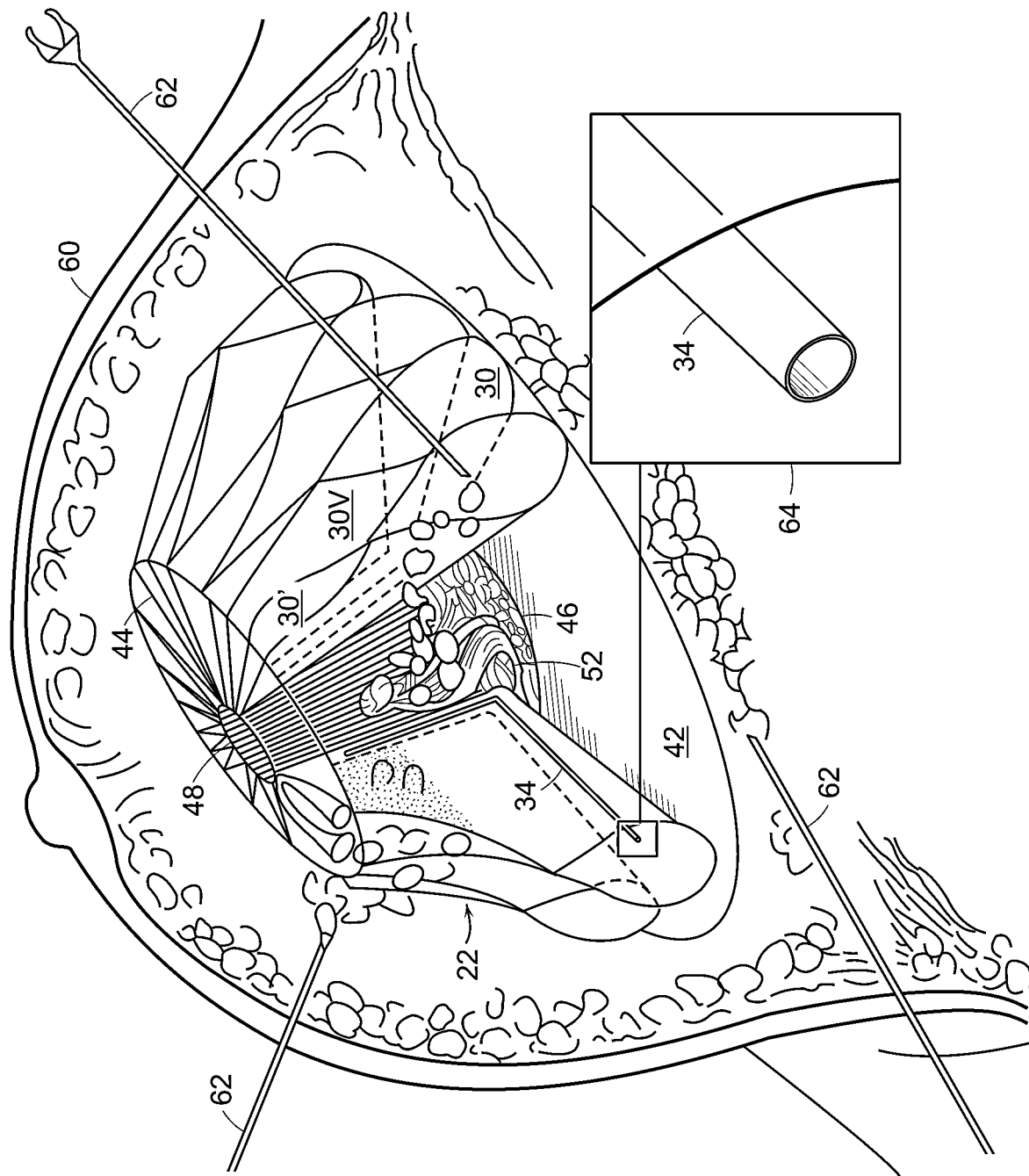
FIG. 5 is a broken perspective view illustrating implant of a tissue engineering device of the present invention in the breast after mastectomy.
Figure 13:
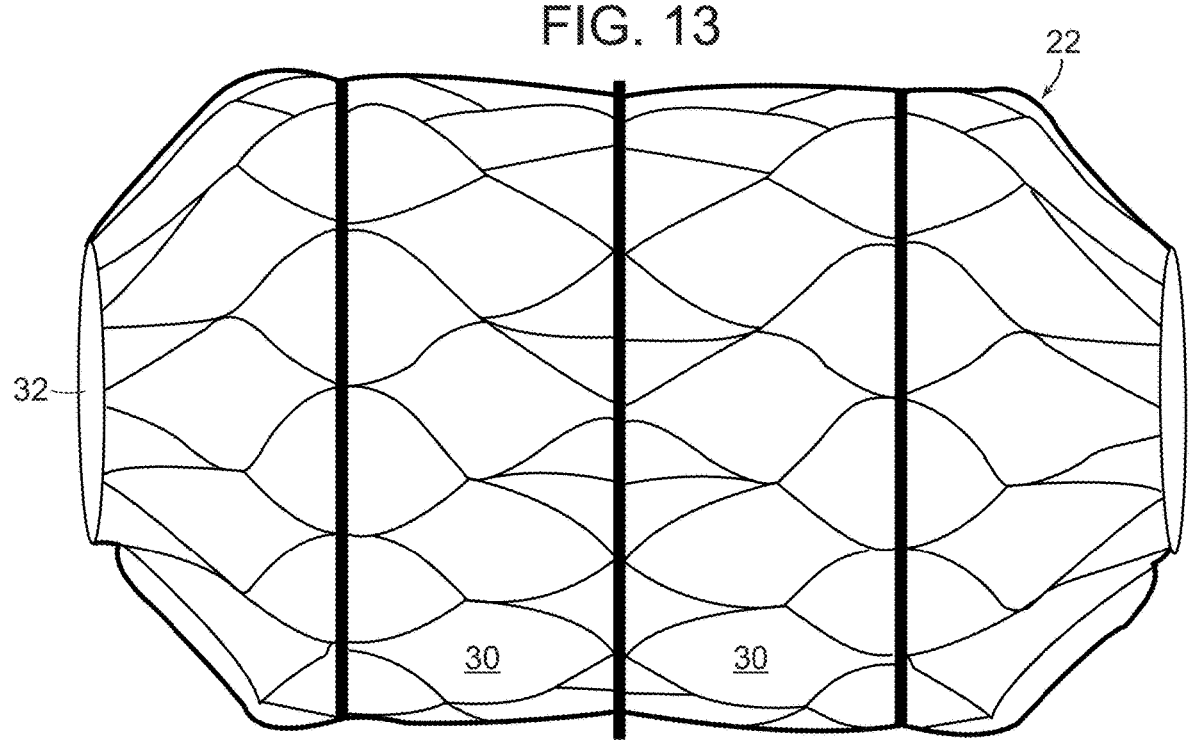
FIG. 13 is a side view of a tissue engineering device of the present invention having a tubular configuration.
Figure 14:
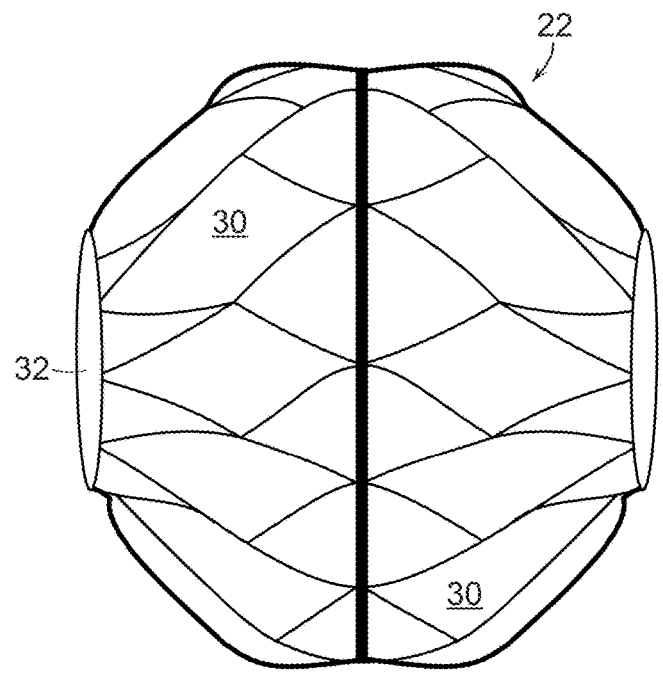
FIG. 14 is a side view of a tissue engineering device of the present invention having a spherical-like configuration for implant after a lumpectomy.

The scaffold can be made of one or more pleated sheets of mesh absorbable material or can be molded of porous absorbable material to be unitary in nature as described above. A segment 36 of the absorbable material forming the side wall 28 is shown in FIG. 3. The pleated sheets of absorbable material are folded as shown at the bottom 38 to form the tissue engineering chambers 30, each of which is defined by opposing panels 39 extending from the bottom to form interior walls. Adjacent sheets or panels of absorbable material can be fixed or connected as shown at 40 to form sub-segment tissue engineering chambers 30' and 30". If the scaffold is not molded or otherwise unitarily formed, the connection shown at 40 can be achieved by welding to attach all points of contact in the structure. The connection of adjacent tissue engineering chambers creates a contiguous outer surface for the scaffold and stabilizes the compression and tensioning forces exerted on the scaffold by bodily tissue to achieve a floating equilibrium or tensegrity via the non-rigid tissue engineering chambers. Once fat has grown into the tissue engineering chambers, the fat will cooperate with the structure of the scaffold to create biotensegrity. The struts 34 are used if extra support is required due to the weight of tissue in the scaffold, and preferably the struts should terminate below the end surface of the distal portion and not extend beyond the perimeter of the disc surface of the proximal portion. Additional tissue engineering chambers 30V are formed in the spaces between panels 39 of adjacent tissue engineering chambers. Accordingly, the aggregate surface area of the mesh absorbable material provided by the tissue engineering chambers will be substantially greater than the fascia surface area in the anatomical space in which the tissue engineering device is implanted as can be seen in FIGS. 4 and 5. As noted above, the tissue engineering chambers 30 are formed or divided into sub-segments 30' and 30", and the sub-segments increase the stability of shape of the scaffold, due to tensegrity, and support the over-all volume of adipose tissue engineering required to perform breast reconstruction. The tissue engineering chambers each, desirably, generates an average of 5 cc of adipogenesis such that a scaffold having fifty tissue engineering chambers allows the transplant of 250 cc with no fat necrosis. In the scaffold employed in the tissue engineering device embodiment of FIG. 1, the chambers 30 would hold 7 ccs of fat, the chambers/sub-segments 30' would hold 5 ccs of fat and the chambers/sub-segments 30" would hold 3 ccs of fat. The number of tissue engineering chambers/sub-segments depends on the stability provided by the L-shaped struts and the amount of absorbable material desired. The tissue engineering chambers/sub-segments are each arranged in a ring such that the scaffold is formed of a plurality of rings of tissue engineering chambers to form various geometric configurations for the scaffold. Looking at FIG. 2, tissue engineering chambers 30 form an outer ring, tissue engineering chambers 30' form an intermediate ring and tissue engineering chambers 30" form an inner ring. For example, the plurality of rings can be arranged in tiers having decreasing diameters such that the sidewall 28 is tapered and the scaffold has a frustoconical-like configuration. Where the plurality of rings has substantially the same diameter, the scaffold will have a tubular/cylindrical configuration as shown in FIG. 13. Hemispherical-like and spherical-like configurations can be achieved by varying the diameter of the rings. A spherical-like configuration can also be achieved by securing two hemispherical-like scaffolds together as shown in FIG. 14. The proximal portion 24 of the scaffold has a disc-like end surface 42 and the distal portion 26 of the scaffold has a disc-like end surface 44, both end surfaces being made of absorbable material. In the truncated geometrical shape shown in FIG. 1, the end surfaces 42 and 44 are disposed at the base and apex, respectively, of the scaffold and have openings 46 and 48 therein, respectively, aligned with hollow central core 32.

A tissue engineering method according to the present invention will be described in connection with a breast procedure after mastectomy and with reference to FIGS. 4 and 5. It is important that the anatomical space in fascia, i.e. the mastectomy defect, be stented and held open to prevent scar contracture of the wound which is prohibitive to fat regeneration, i.e. adipogenesis. In order for adipogenesis to take place, a low tissue tension is required, and a nearby capillary blood supply is needed. The tissue engineering method comprises the steps of implanting scaffold 22 in the anatomical space in the fascia 50 created during the mastectomy, anchoring the proximal portion of the scaffold in the space 50 with the proximal end disc-like surface abutting the fascia, inserting autologous tissue, normally autologous liposuctioned fat, in the tissue engineering chambers 30, pulling a vascular flap pedicle 52 along with the blood vessels (perforator 54 shown in FIG. 4) into the hollow inner region 29 of the scaffold formed by the hollow core 32 and positioning the vascular flap pedicle in the distal portion of the scaffold to position the blood vessels 54 along the hollow inner region to provide capillary blood supply to the autologous tissue in the tissue engineering chambers 30. For breast procedures, the vascular flap pedicle is dissected from a small pectoral muscle island flap having a perforator coming from the thoracoacromial artery, and the perforator/vascular flap pedicle is accessed by instruments passed through the opening 48 in the disc-like end surface 44 of the distal portion 26. A forceps 56 is shown grasping a suture 58 tied around the vascular flap pedicle. Accordingly, blood vessels can be pulled by the suture through the central hollow core from the base up through the apex at the time of implant of the scaffold and the suture can be tied to the apex of the scaffold to anchor the vascular flap pedicle in place before the scaffold is sutured to surrounding fascia in the anatomical space 50 to prevent rotation or displacement of the scaffold in the anatomical space. The autologous tissue inserting step can be performed prior to implant of the scaffold, after implanting of the scaffold or prior to and after implant of the scaffold. The tissue engineering method can be enhanced by creating negative pressure in the scaffold and by filling the tissue engineering chambers with loose felt cellulose matrix prior to inserting fat.

FIG. 5 shows a scaffold 22 according to the present invention implanted in a space 50 after mastectomy within a breast with the scaffold having fewer tissue engineering chambers 30 than the scaffold shown in FIGS. 1 and 4 and illustrates cannulas 62 for injecting microglobules of the fat, approximately 1 to 1.5 mm in diameter, between the skin envelope and the scaffold 22, under the scaffold and near the chest wall and into the tissue engineering chambers 30 and 30'. Granulation tissue, a collagen and extra cellular protein matrix created by fibroblasts mixed with rich capillary growth emanating from the pectoral muscle vascular flap/perforator 52 in the hollow core 32 of the scaffold, is generated in the center of the scaffold to create centrally located supportive vascular tissue which is mimicked by tissue growing in from the peripheral surfaces and from the surrounding superficial fascia remnants from the mastectomy dissection. Accordingly, the surfaces of the mesh absorbable material, which is segmented to form the tissue engineering chambers, have vascular supported tissue ingrowth from the outside in and from the inside out producing a large vascularized absorbable mesh scaffold that can sustain adipogenesis. The termination of the struts 34 to not extend beyond the perimeter of the base of the scaffold is shown at 64.

Figure 6:
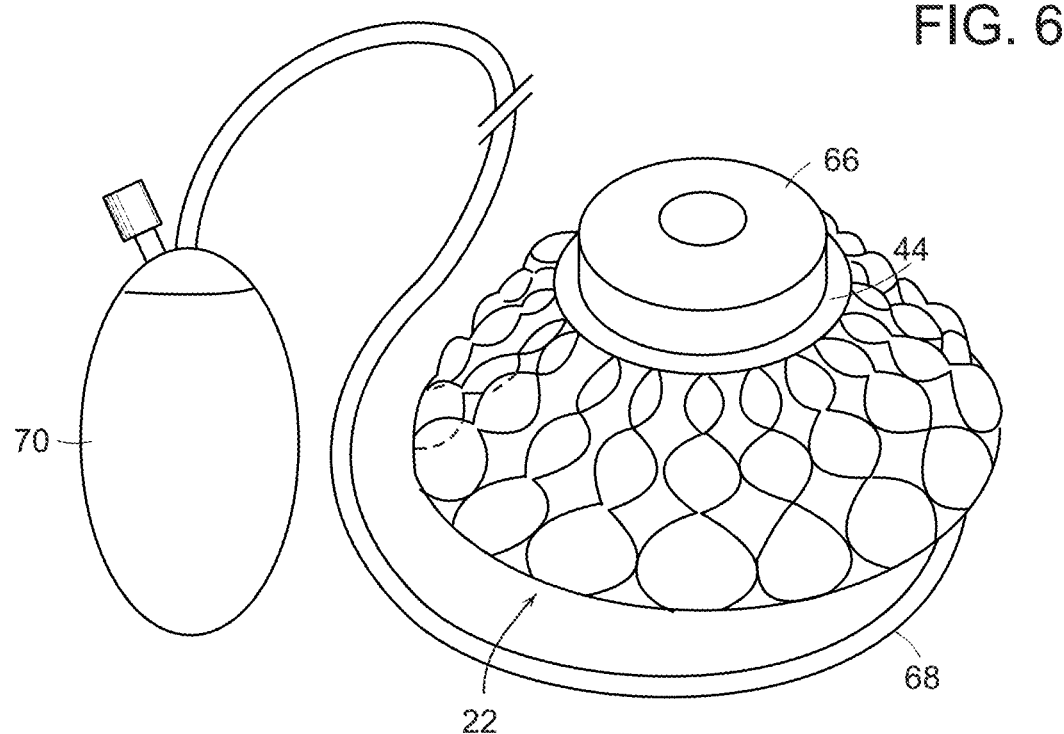
FIGS. 6 and 7 are top perspective and bottom plan views, respectively, of a tissue engineering device of the present invention modified to include a layer of absorbable material on a disc-like distal end surface and detachable tubing on a disc-like proximal end surface.
Figure 7:
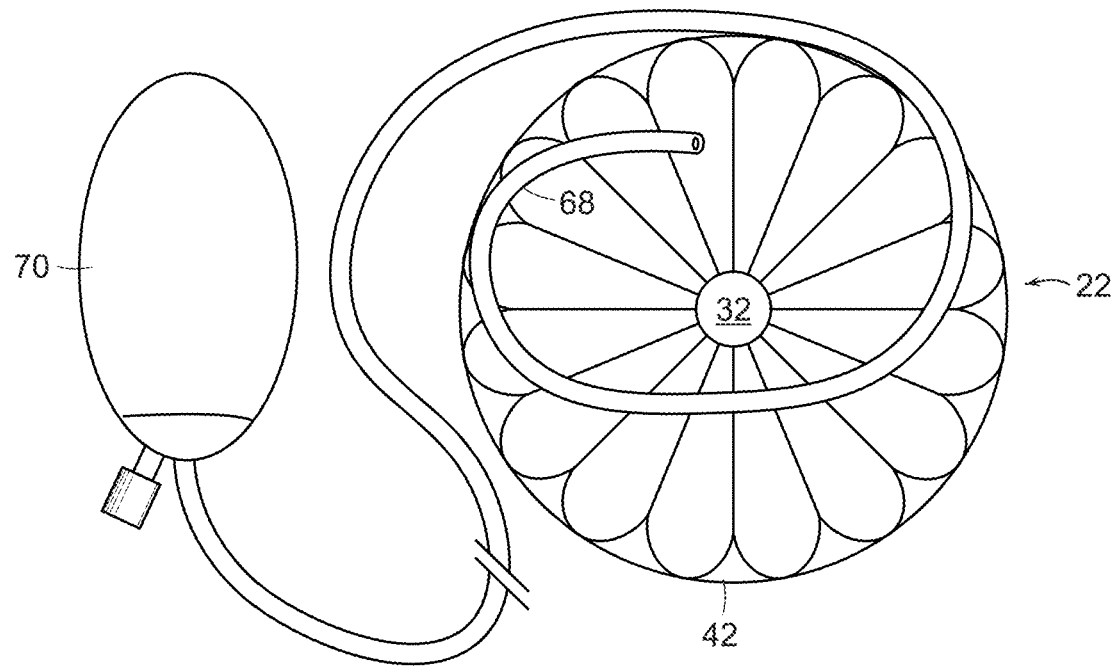
Figure 8:
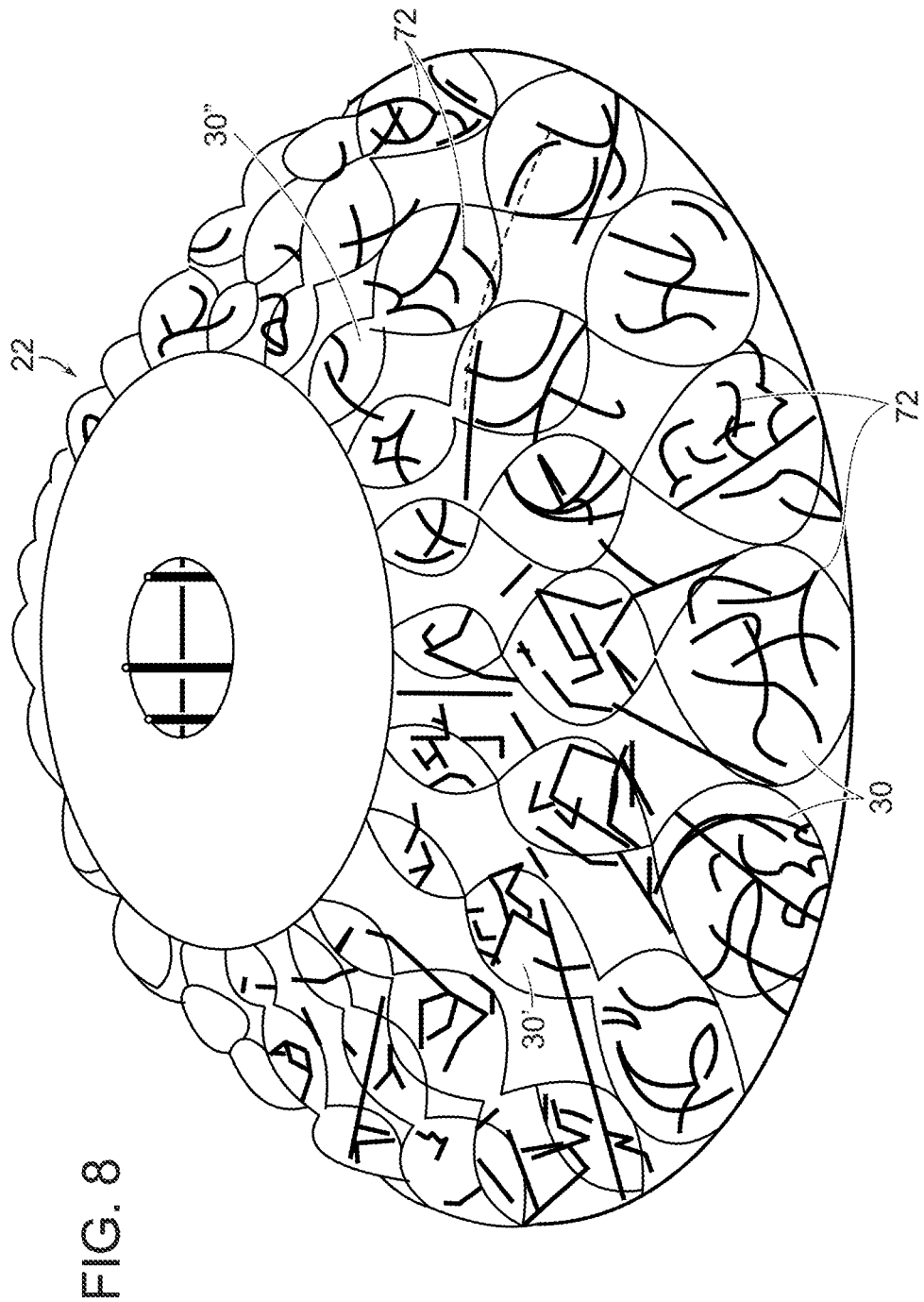
FIG. 8 is a perspective view of a tissue engineering device of the present invention with short term absorbable material in the tissue engineering chambers.

FIGS. 6, 7 and 8 show modifications of the tissue engineering device 20 shown in FIG. 1. FIG. 6 shows a layer of cellulose matrix 66, such as methyl cellulose, disposed on the distal end disc-like surface 44 having a thickness of approximately 1 cm. Fat is injected in the layer, and the layer acts as a separation of the areolar dermis from the scaffold to facilitate lifting the skin envelope and nipple areolar dermis away from the scaffold during subsequent fat grafting, if required. FIG. 7 shows tubing 68 with holes therein detachably carried on the proximal portion disc-like end surface 42 communicating with a small suction pump 70 to create negative pressure in the scaffold and to drain excess fluid. The tubing 68 is also shown in FIG. 6.

FIG. 8 shows the application of a loose felt of cellulose matrix 72, such as methyl cellulose, to the mesh absorbable material forming the tissue engineering chambers 30, 30' and 30" of the scaffold. The loose felt greatly increases the surface area of the mesh absorbent material but will dissolve much faster since the absorbable material used to fabricate the scaffold is considered to be a long term absorbable material relative to the cellulose matrix which is considered to be a short term absorbable material. The cellulose fibers of the cellulose matrix will additionally hold fat globules in place and also act as an additional surface for capillary ingrowth.

Figure 9:
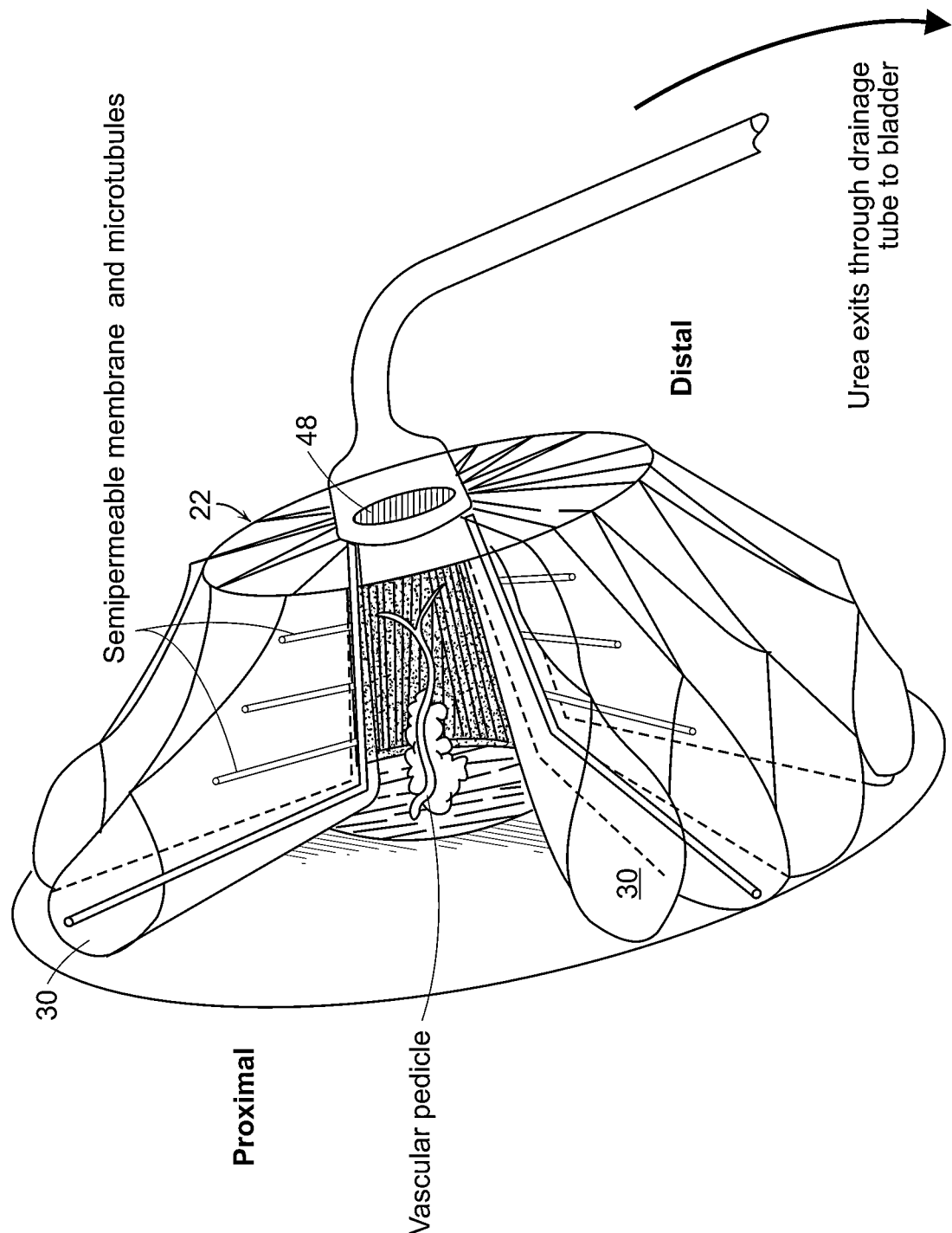
FIGS. 9 and 10 are broken perspective views of a tissue engineering device of the present invention used for supplementing kidney function.
Figure 10:
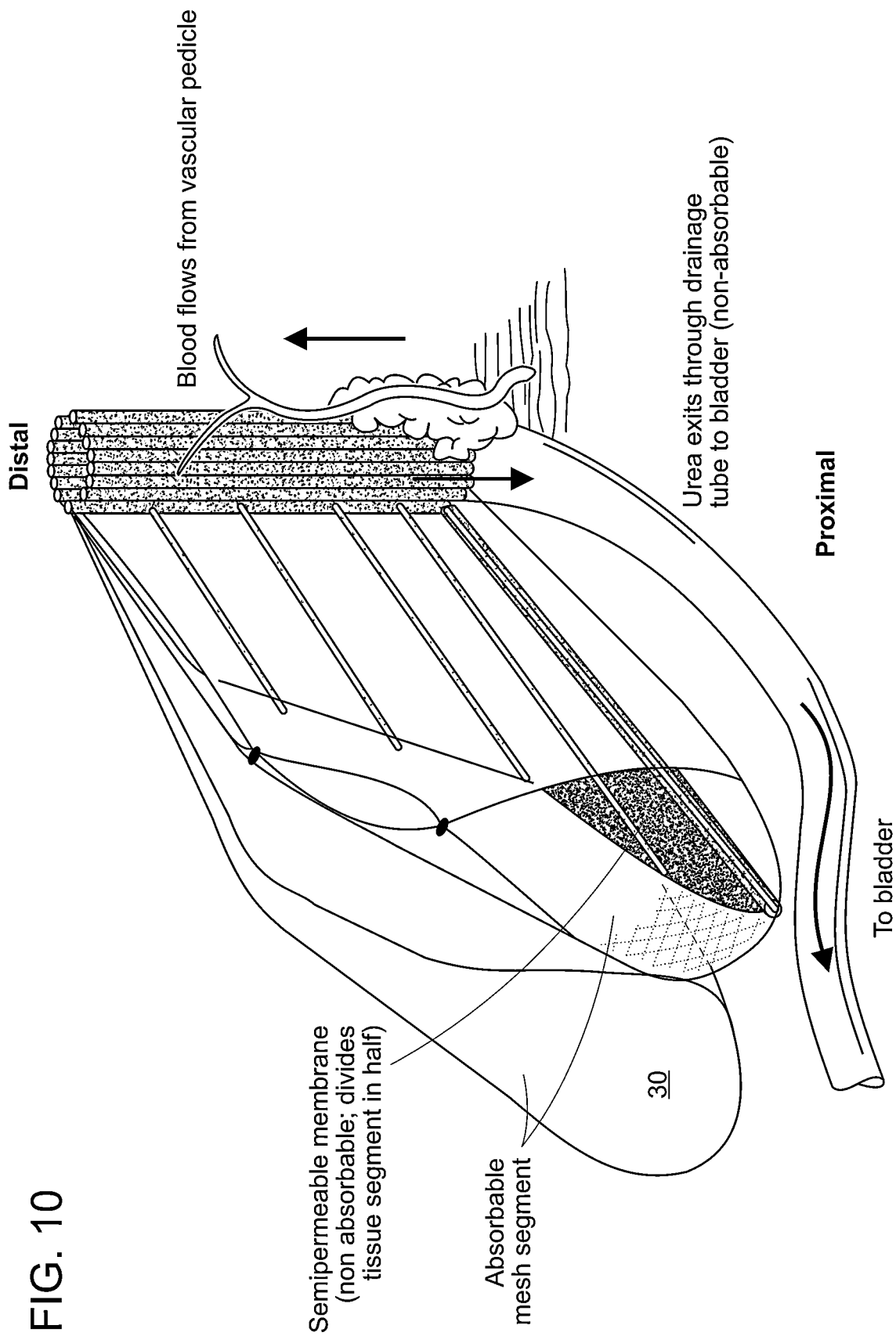

A modification of the tissue engineering device of FIG. 1 to provide a kidney-type function is shown in FIGS. 9 and 10 with parts labeled to explain their function. The scaffold 22 has essentially the same structure as the scaffold shown in FIG. 5 with the addition of microtubules in semipermeable membranes disposed in the chambers 30 dividing the chambers in half. In FIG. 9, a tube communicates with the hollow central core at the opening 48 in the disc-like end surface of the distal portion of the scaffold for exit of urea to permit drainage to the bladder. In FIG. 10, urea exits from the proximal portion of the scaffold.

Figure 11:
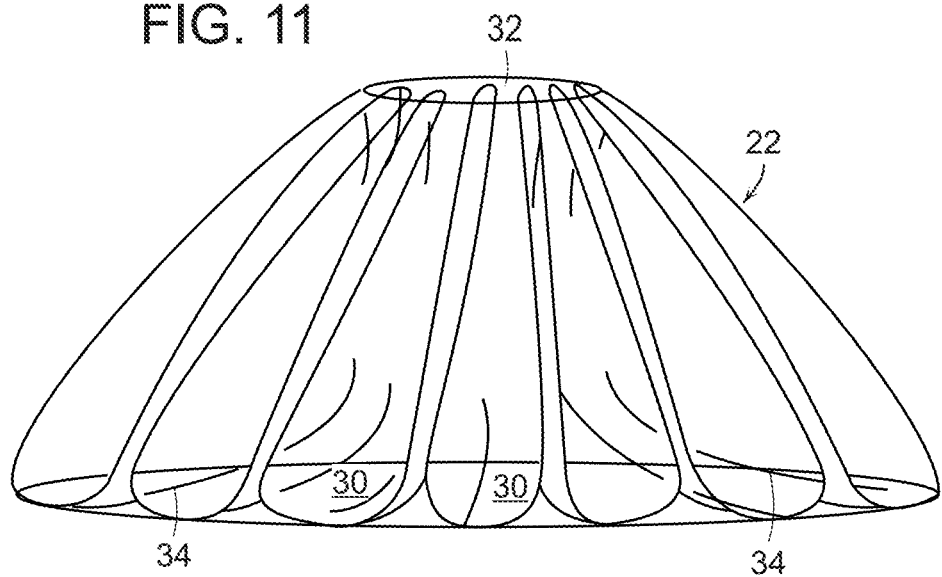
FIGS. 11 and 12 are side views of tissue engineering devices of the present invention having varying profiles.
Figure 12:
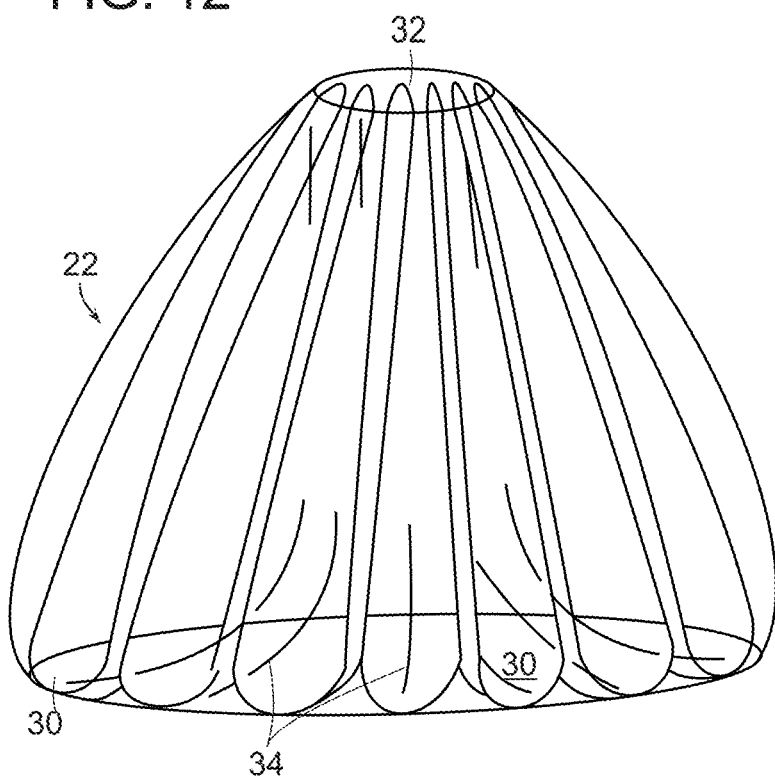

Embodiments of scaffolds 22 for use in the tissue engineering device of the present invention are shown in FIGS. 11 and 12 where the tissue engineering chambers 30 are not formed with sub-segments. The interior hollow core 32 and the L-struts 34 are covered by rugose draping sheets of mesh absorbable material. The embodiment shown in FIG. 11 has a base wider than its height and would be covered with liposuctioned fat whereas the embodiment shown in FIG. 12 has a height greater than the width of its base and would be implanted behind the breast gland (corpus mammae) to effect increased projection of the breast. These embodiments can be used in instances of breast reduction and mastopexy after implantation. The patient's cells, including fibroblast producing collagen and capillaries grow into the scaffold and create an engineered fascia-like tissue which persists after the mesh fibers are absorbed.

The embodiment of the scaffold 22 shown in FIG. 13 is tubular and essentially cylindrical and would be employed in tissue engineering devices used with filter-type organs. The hollow central core 32 runs the length of the cylindrical scaffold. When used for the kidneys, two-dimensional circular discs, which are the semipermeable membranes containing the microtubule collecting ducts, are spread out along the longitudinal axis of the scaffold at regular intervals. Flanked on either side of each semipermeable membrane are the absorbable material chambers/segments 30 where the engineered adipose tissue grows. The adipose tissue gets blood supply by the vascular flap pedicle (in the case of use with the kidneys, the inferior epigastric artery) which is dissected out of the muscle in the lower abdomen, then pulled through the central core. The drainage tube shown in FIGS. 9 and 10 collects urine and runs from the distal to proximal ends, where it is then tunneled to the bladder like a ureter.

A spherical-type scaffold 22 is illustrated in FIG. 14 and would be of a size smaller than scaffolds used for total breast reconstruction following mastectomy. The embodiment of FIG. 14 is designed for use to reconstruct partial mastectomies, otherwise known as lumpectomies. The diameter of the spherical-type scaffold would normally be between 2.5 cm and 5 cm, and the central hollow core 32 would normally have a diameter of approximately 1 cm and facilitates tissue ingrowth and expedites absorption. The spherical-type scaffold for use after a lumpectomy would not require any fat grafting or use of vascular perforator pedicles due to the large ratio of surface area to volume which insures rapid ingrowth of tissue. The spherical-type scaffold will hold apart remaining tissue that surrounds a lumpectomy defect and prevent collapse and scarring. The negative pressure of the anatomical lumpectomy space induces tissue ingrowth and adipogenesis in the same manner as the tissue engineering chambers previously described without the need for fat grafting. A fractal version of the spherical-type scaffold can be on the order of 1 to 1.5 mm to permit injection as filler into existing superficial fascia and would be replaced by tissue and fat from adipogenesis without the need for liposuction and fat grafting. In order to achieve a desired aesthetic outcome following lumpectomy, the small spherical-type scaffold is implanted and fills the defect to promote gradual healing of the lumpectomy space without scar contracture. The spherical-type scaffold acts as a stent against wound contracture and scarring and promotes M2 regenerative healing of the lumpectomy defect. The spherical-type scaffold includes a plurality of tissue engineering chambers connected with one another as previously described to present a contiguous periphery to fill the defect. Titanium micro-clips can be mounted to the surface of the spherical-type scaffold to define its location for post-lumpectomy breast procedures and mammograms. Due to the small size of the spherical-type scaffold, which will have a diameter between 2.5 and 5 cm, the scaffold will typically have only 12 segments with only 24 subsegments. Each subsegment will have an approximately 5 cc volume.

The tissue engineering device of the present invention can be implanted in various locations of the body particularly in anatomical spaces in the fascia, both in the superficial fascia and the deep fascia. The scaffold of the tissue engineering device can have any shape or size dependent upon the anatomical space in fascia and the functional requirements of the scaffold (for example, for breast reconstruction after mastectomy, for cosmetic or aesthetic purposes relating to the breast or other soft tissue, such as the buttocks, or for various functional organs of the body). Accordingly, the scaffold would be smaller in size and essentially spherical in shape for lumpectomies. The scaffold can be placed in a space in the body created by surgical dissection to divide the space into segments and sub-segments. The surfaces of the scaffold invite tissue ingrowth consisting of fibroblasts making collagen fibers which surround the polymer filaments of the absorbable material and capillary vascular ingrowth. The spaces between the pleats/chambers leave room for new adipose tissue creation, through a process mediated by mechanical signals, due to low tissue tension created by holding the surgical dissection apart with the scaffold. This stimulates stromal cells in the fascia to secrete protein "cytokines" such as CXCL12 which attracts stem cells from circulation to migrate and congregate in the space occupied by the tissue engineering device. As a result, a healthy, well vascularized engineered tissue results in the location of implantation of the tissue engineering device. The absorbable material scaffold can be covered with various chemical compounds, cells, and proteins prior to implantation, depending on various regenerative therapeutic goals. The tissue engineering device thus becomes an in vivo bioreactor acting as a repository for genetically repaired, autologous patient cells, or allograft donor cells, that have been genetically altered or repaired, e.g. for example, with CRISPR technology. Once cells have been genetically modified in vitro, the cells are transplanted into the tissue engineering device bioreactor environment, where the cells find an incubator environment for growth and are exposed to a rich circulation which can send the products of the repaired cell line into the patient's blood stream. One example is the treatment of diabetes. Type I diabetics have an inadequate number of functioning pancreatic islet cells, which make insulin. The beta cells of the pancreatic islets secrete insulin and play a significant role in diabetes. Repaired autologous beta cells or allograft beta cells can be transplanted into the tissue engineering device for the treatment of diabetes. The tissue engineering device can be placed anywhere within the fascia system of the body, but most conveniently at locations such as the lower lateral abdominal region, posterior hip region above the buttocks, or the upper chest, just below the clavicle. These locations allow implantation via outpatient minor surgical procedures, using local anesthesia and mild sedation.

The porosity of the porous absorbable material from which the scaffold is made will be determined based on its area of use in the body. Porosity is important to the reaction of the tissue to the scaffold. Macroporous mesh absorbable materials that have large pores facilitate entry of micro-phages, fibroblast and collagen fibers that constitute new connective tissue. Microporous mesh absorbable materials, with pores less than 10 micrometers, have shown a higher rejection rate due to scar tissue rapidly bridging the small pores. Though there is no formal classification system for pore size, in most instances the scaffold will be made of a macroporous mesh absorbable material with pores greater than 10 micrometers.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An implantable prosthesis comprising:
a three-dimensional, tissue infiltratable body made of biocompatible material having a proximal end and a distal end spaced from the proximal end, the body having a longitudinal axis from the proximal end to the distal end, the body including:
a plurality of chambers arranged circumferentially about the longitudinal axis, the plurality of chambers arranged to face in an outward radial direction oriented transverse to the longitudinal axis, the plurality of chambers including at least a first chamber, a second chamber and a third chamber which are different from each other, the first chamber and the second chamber being located adjacent each other in a circumferential direction about the longitudinal axis, the third chamber being located above or below the first chamber in an axial direction oriented along the longitudinal axis, a side of the first chamber being connected to a side of the second chamber, the third chamber being connected to a top or bottom of the first chamber.

2. The implantable prosthesis according to claim 1, wherein the body is configured to augment and/or reconstruct an anatomical shape of a human breast.

3. The implantable prosthesis according to claim 1, wherein, the plurality of chambers are arranged and connected to stabilize compression and tension forces exerted on the scaffold by tissue and/or muscle when implanted in a human body.

4. The implantable prosthesis according to claim 1, wherein each of the plurality of chambers extends along a corresponding chamber axis which is transverse to the longitudinal axis.

5. The implantable prosthesis according to claim 4, wherein each chamber axis extends in a different radial direction relative to each other.

6. The implantable prosthesis according to claim 5, wherein the chamber axis of each of the plurality of chambers is oriented at an angle relative to the proximal end, the angle of the chamber axis being the same for each chamber in a first group of chambers.

7. The implantable prosthesis according to claim 6, wherein the angle of the chamber axis of the first group of chambers is different from the angle of the chamber axis of a second group of chambers.

8. The implantable prosthesis according to claim 4, wherein each of the plurality of chambers is open in the corresponding outward radial direction.

9. The implantable prosthesis according to claim 1, wherein each of the plurality of chambers has a size which increases in the outward radial direction.

10. The implantable prosthesis according to claim 9, wherein each of the plurality of chambers has a width which increases in the outward radial direction.

11. The implantable prosthesis according to claim 1, wherein the body has a frusto-conical shape.

12. The implantable prosthesis according to claim 1, wherein the body has a spherical shape.

13. The implantable prosthesis according to claim 1, wherein the body has a tubular shape.

14. The implantable prosthesis according to claim 1, wherein the body has a planar configuration at the proximal end and/or the distal end.

15. The implantable prosthesis according to claim 1, further comprising a first layer of biocompatible material located at the proximal end of the body and a second layer of biocompatible material located at the distal end of the body.

16. The implantable prosthesis according to claim 1, wherein the body is formed of absorbable material.

17. The implantable prosthesis according to claim 1, wherein the body is formed of mesh fabric.

18. The implantable prosthesis according to claim 17, wherein the body includes a plurality of sheets of mesh fabric.

19. The implantable prosthesis according to claim 18, wherein the plurality of sheets of mesh fabric are connected together to form the plurality of chambers.

20. The implantable prosthesis according to claim 1, wherein the plurality of chambers are tissue infiltratable.

* * * * *